United States Patent [19]

Weil

[11] 4,145,547
[45] Mar. 20, 1979

[54] UREIDOALKYLPHOSPHONATES AND THEIR USE FOR THE FLAMEPROOFING OF TEXTILES

[75] Inventor: Edward D. Weil, Hastings-on-Hudson, N.Y.

[73] Assignee: Stauffer Chemical Company, Westport, Conn.

[21] Appl. No.: 800,975

[22] Filed: May 26, 1977

Related U.S. Application Data

[62] Division of Ser. No. 356,526, May 2, 1973, Pat. No. 4,044,006, which is a division of Ser. No. 50,304, Jun. 26, 1970, Pat. No. 3,763,281.

[51] Int. Cl.$^2$ .................. C07D 233/02; C07D 239/04; C07D 251/04
[52] U.S. Cl. ..................................... 548/320; 548/319; 544/214; 544/243
[58] Field of Search ................... 548/320, 319; 544/67, 544/214; 260/251 R

[56] References Cited

U.S. PATENT DOCUMENTS

| | | | |
|---|---|---|---|
| 3,627,767 | 12/1971 | Nachbur et al. | 260/256.5 R |
| 3,654,169 | 4/1962 | Matzner et al. | 252/580 |
| 3,658,804 | 4/1972 | Petersen et al. | 548/320 |
| 3,763,281 | 10/1973 | Weil | 260/932 |
| 4,044,006 | 8/1977 | Weil | 544/67 |
| 4,085,283 | 4/1978 | Otter et al. | 544/214 |

FOREIGN PATENT DOCUMENTS

2433372 1/1976 Fed. Rep. of Germany ........... 544/214

OTHER PUBLICATIONS

Ivanov et al., Index Chemicus, vol. 33, Abst. No. 112548 (5/19/69).
Shokol et al., Chem. Abstracts vol. 72, Abst. No. 2956b (1970) (abstract of the original article, Dopov. Akad. Nauk Ukr. RSR, Ser. B 1969, pp. 818 to 821).
Petersen, Liebigs Ann. Chem. vol. 726, pp. 89 to 99 (1969).
Medved et al., Chem. Abstracts vol. 51, cols. 1817–1818 (1957) (abst. of Izvest. Akad. Nauk S.S.S.R. Otdel Khim. Nauk 1956, pp. 684–691).

Primary Examiner—John D. Randolph
Attorney, Agent, or Firm—Daniel S. Ortiz

[57] ABSTRACT

Novel ureidoalkylphosphonates, methods for their prepration as well as for their use in preparing durable, flameproof finishes for textiles are disclosed. These ureidoalkylphosphonates are found to be low in cost, readily prepared and of minimal toxicity.

2 Claims, No Drawings

UREIDOALKYLPHOSPHONATES AND THEIR USE FOR THE FLAMEPROOFING OF TEXTILES

This is a division of Several No. 356,526 filed May 2, 1973 now U.S. Pat. No. 4,044,066, which in turn is a division of Ser. No. 50,304 filed June 26, 1970, now U.S. Pat. No. 3,763,281.

BACKGROUND OF THE INVENTION

The condensation products of formaldehyde with ureas are well known substances widely employed to prepare thermoset resins which find a multitude of uses as adhesives, coatings, binders, and as finishes for paper, wood and textiles.

Urea-formaldehyde resins are in themselves rather incombustible. However, when they are applied to combustible substrates such as paper, cloth, wood, or the like, the resulting combination is often highly combustible. It has been known that the addition of such phosphorus containing additives as phosphoric acid, ammonium phosphate and the like markedly reduces the flammability of the products resulting from the combination of urea-formaldehyde resins with combustible substrates. However, such additives are readily removed upon even a minimal leaching with water. Thus, for uses where resistance to water is necessary as in coatings, apparel fabrics, paper, wood, plywood, and the like, these additives do not provide sufficiently durable, flame-retarding compositions.

The literature describes previous attempts to prepare urea derivatives having organic phosphorus groups attached to the nitrogen atoms of the urea, e.g. U.S. Pat. No. 3,393,253. However, the resulting compounds have direct phosphorus-to-nitrogen bonds which results in their having less than the desired degree of hydrolytic stability. Moreover, such compounds must be made through the use of the dangerously unstable N-chlorourea intermediate.

It is, therefore, the prime object of this invention to provide stable, urea derivatives having organically bound phosphorus substituted thereon. It is a further object to provide phosphorus substituted urea derivatives useful for conducting condensation or co-condensation reactions which yield aminoplastic resins having utility as durable flame retardant coatings, binders, adhesives, and finishes for various substrates including textiles and paper as well as for use as molding resins. It is still another object to make available new processes for preparing these phosphorus containing urea derivatives. Various other objects and advantages of this invention will be apparent from a reading of the disclosure which follows hereinafter.

Technical Disclosure of the Invention

It has now been discovered that a novel class of inexpensive, non-toxic ureidoalkylphosphonates may be conveniently prepared, these derivatives being capable of providing durable flame retardant finishes for a variety of flammable substrates and particularly for textiles.

The novel compounds of this invention correspond to the structural formula:

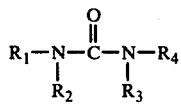

where $R_1$, $R_2$, $R_3$ and $R_4$ are selected from the group consisting of: hydrogen; hydroxymethyl; $C_1$-$C_{12}$ alkoxymethyl; methylene conjoining two urea nuclei having substituents as here defined and a phosphonate group Z where Z corresponds to the formula:

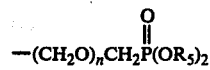

in which n is an integer having a value of from 0 to 1 and $R_5$ is selected from the group consisting of $C_1$-$C_{12}$ alkyl, allyl, $C_1$-$C_{12}$ 2-chloroalkyl and $C_1$-$C_{12}$ 2-hydroxy-alkyl groups; where $R_2$ and $R_3$ can be conjointly equal to $-CH_2CH_2-$, $-CH_2CH_2CH_2-$, $-CH_2OCH_2-$, $-CH_2N(C_1-C_{12}\ alkyl)CH_2-$ and $-CHOHCHOH-$ groups; where $R_2$ and $R_3$ can be conjointly equal to a

group in which the free valences of each carbon atom in said

group comprise the $R_2$ and $R_3$ groups of a second urea nucleus corresponding to the structure:

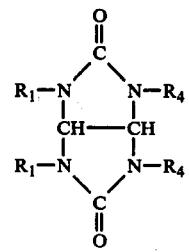

with the proviso that at least one and no more than three of said $R_1$, $R_2$, $R_3$ and $R_4$ groups are Z groups and that at least one of said $R_1$, $R_2$, $R_3$ and $R_4$ groups is selected from the group consisting of hydrogen, hydroxymethyl, $C_1$-$C_{12}$ alkoxymethyl, and $-CHOHCHOH-$ groups.

The above described ureidoalkylphosphonates may be prepared by means of various reaction procedures depending upon their precise composition. Thus, for example, where n in the above given structural formula is to be O, the urea intermediate used as starting material should contain the $R_1$, $R_2$, $R_3$ and $R_4$ groups which are desired in the end product except that in the position(s) in the end product which is (are) to be substituted with a Z group, the urea intermediate will have a hydroxymethyl, i.e. a methylol group. The selected urea intermediate is then caused to react in the liquid phase at 0 to 180° C. with at least one molar equivalent of a trialkyl phosphite having the formula $P(OR_5)_3$, where $R_5$ is defined above, until substantially one molar equivalent of an $R_5OH$ alkanol by-product is released or substantially no further trivalent phosphorus remains detectable.

Surprisingly, this process yields the phosphonate structure $-N-CH_2P(OR_5)_2$ instead of the phosphite structure $-N-CH_2-O-P(OR_5)_2$ which would be expected to be produced under these conditions by means of a simple transesterification. This procedure will, hereinafter, be referred to as "Process No. 1".

Alternatively, if the starting urea intermediate in Process No. 1 contains a $C_1-C_{12}$ alkoxymethy rather than a Z group, it can be reacted, in the liquid phase at 0 to 180° C., with at least one molar equivalent of a dialkyl phosphonate having the formula

until substantially one equivalent of an alkanol has been evolved or until no further H-P compound can be detected in the reaction mixture. This procedure will, hereinafter, be referred to as "Process No. a." It is to be noted that Processes Nos. 1 and 1a may be conducted with a mixture of two or more urea intermediates and/or trialkyl phosphites and/or dialkyl phosphonates.

In still another reaction procedure, where n in the ureidoalkylphosphonate is to be 1, the urea compound used as the starting intermediate should contain the $R_1$, $R_2$, $R_3$ and $R_4$ groups which are desired in the end product except that where there is to be a Z group in the end product, the starting urea intermediate should contain a hydroxymethyl, i.e. a methylol, group or a $C_1-C_{12}$ alkoxymethyl group. The selected urea intermediate is then caused to react, in the liquid phase, at 20-180° C. with at least one molar equivalent of a dialkylphosphonate having the formula

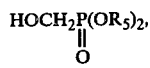

preferably in the presence of an acid catalyst such, for example, as sulfuric acid, p-toluenesulfonic acid, phosphoric acid, or the like, until substantially one molar equivalent of water, in the case of a starting urea having a methylol methyl group, or one molar equivalent of alkanol, in the case of a starting urea having a $C_1-C_{12}$ alkoxymethyl group, has been evolved. The latter procedure is, hereinafter, to be referred to as "Process No. 2." It is to be noted that it may be conducted with a mixture of two or more urea intermediates and/or dialkylphosphonates.

There is another useful process, hereinafter referred to as "Process No. 3," for preparing those compositions of this invention wherein the $R_1$, $R_2$, $R_3$, and $R_4$ groups are to be selected from the group consisting of $C_{1-C12}$ alkoxymethyl, methylene conjoining two urea nuclei or where $R_2$ and $R_3$ are conjointly $-CH_2CH_2-$, $-CH_2CH_2CH_2-$, $-CH_2OCH_2-$ or

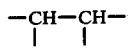

groups in which the free valences of the last named radical are joined to a second urea nucleus, and where at least one of $R_1$, $R_2$, $R_3$ or $R_4$ is a phosphonate group Z as defined hereinabove wherein n equals zero. This additional method consists of reacting a correspondingly substituted urea intermediate, having a $C_1-C_{12}$ alkoxymethyl group at the site to be occupied by Z, with a dialkyl phosphorochloridite of the type $(R_5O)_2PCl$ or with an amount of trialkyl phosphite of the formula $(R_5O)_3P$ along with $PCl_3$ equivalent to the amount of the phosphorochlorodite. The trialkyl phosphite is first preferably added to the urea intermediate followed by the addition of the $PCl_3$. The reaction is carried out at a temperature of about $-20$ to 180° C. and preferably at about 0 to 120° C. and for a period of from about one minute to about 50 hours depending on the temperature. In general, the reaction mixture is maintained at the reaction temperature until trivalent phosphorus is no longer detectable whereupon it is stripped of the alkyl chloride by-product.

This method is especially suitable, for example, for making compositions of the type

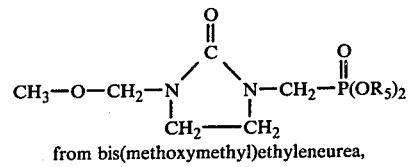

from bis(methoxymethyl)ethyleneurea,

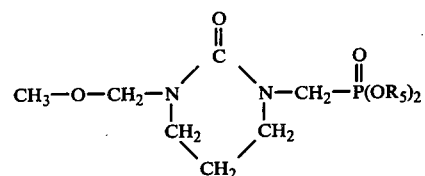

from bis(methoxymethyl)propyleneurea and

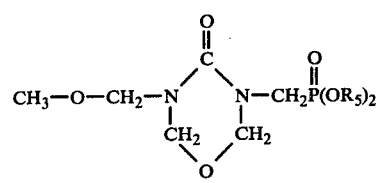

from bis(methoxymethyl)uron.

Where any of the $R_1$, $R_2$, $R_3$, or $R_4$ groups in the final ureidoalkylphosphonate are to be hydroxymethyl, $C_1-C_{12}$ alkoxymethyl, $-CHOHCHOH$, $-CH_2OCH_2$, $-CH_2N(C_1-C_{12}$ alkyl$)CH_2$- or $<CHCH>$, there are two procedures which can be used for preparing such products. Thus, either such group(s) can be present in the initial urea intermediate prior to the formation of the phosphonate group Z, or, alternatively, the urea intermediate can contain hydrogen in place of the ultimately desired $R_1$, $R_2$, $R_3$ or $R_4$ groups and the Z group(s) are then introduced by the use of either reaction process No. 1, 1a, or 2 as described above. In addition, the desired $R_1$, $R_2$, $R_3$, and $R_4$ groups can also be introduced by methods which in themselves are well known in the art. For example (a) where introduction of hydroxymethyl groups is desired, an appropriately substituted urea intermediate is reacted with formaldehyde under alkaline conditions; (b) where introduction of $C_1-C_{12}$ alkoxymethyl groups is desired, an appropriately substitute urea intermediate is reacted with formaldehyde under alkaline conditions followed by reaction of the resulting product with a $C_1-C_{12}$ alkanol under acid conditions; (c) where introduction of -CHOHCHOH- groups is desired, an appropriately substituted urea intermediate is reacted with glyoxal; (d) where introduction of $-CH_2OCH_2-$ groups is desired, the intermediate is reacted with at least two molar equivalents of formaldehyde under alkaline conditions whereupon the resulting product is reacted with methanol under acid conditions; (e) where introduction of $-CH_2N(C_1-C_{12}$ alkyl$)CH_2-$ groups is desired, an appropriately substituted intermediate is reacted with two equivalents of formaldehyde and one equivalent of H₂N(C₁-C₁₂ alkyl); and (f) where introduction of <CHCH> groups is desired, an approximately substituted urea intermediate is reacted with ½ molar equivalent of glyoxal under acid conditions.

Suitable urea intermediates for use in the process of this invention include, for example, mono-, di- and trimethylolurea; mono- and dimethylol ethyleneureas or propyleneureas; mono-, di-, tri- and tetramethylolglyoxaldurein; and the alkoxy, especially the $C_1$–$C_{12}$ alkyl ethers, of all of these ureas, bis(methoxymethyl)uron; bis(methoxymethyl)methyltriazone.

Suitable trialkyl phosphites include trimethyl, triethyl, tripropyl, tributyl, triamyl, trioctyl and tridodecyl phosphites; methyl didecyl phosphite; triallyl phosphite; methyl diallyl phosphite; tris-2-hydroxyethyl phosphite and tris-2-chloroethyl phosphite etc.

Suitable dialkyl phosphonates (phosphites) include dimethyl, diethyl, dipropyl, diallyl, methyl allyl, dibutyl, didodecyl, di-2-chloroethyl, di-2hydroxyethyl, and di-2-hydroxypropyl phosphonate, etc.

Suitable dialkylphosphorochlorodites include dimethyl, diethyl, dipropyl, dibutyl, diallyl, bis(2-chloroethyl), dioctyl, methyl ethyl and methyl propyl phosphorochloridite.

Suitable hydroxymethylphosphonates include dimethyl, diethyl, diallyl, dipropyl, didodecyl, di-2-chloroethyl, and di-2-hydroxypropylphosphonate, etc.

Reaction conditions for processes Nos. 1, 1a and 2, as described above, can entail operation at atmospheric pressure, at sub-atmospheric pressure which would aid in stripping off the alcohol or water by-product or at superatmospheric pressure. The reactants may be brought together without a solvent or one can utilize a solvent which will not interfere with the reaction such, for example, as an alcohol, a hydrocarbon, an ether, an ester, a chlorinated hydrocarbon, or a nitrile.

Process No. 1 proceeds without a catalyst although it can be accelerated by adding a catalytically effective concentration of a base such as sodium methylate or sodium carbonate. Process 1a generally does not require the use of any catalyst. On the other hand, process No. 2 proceeds best with an effective concentration of an acid catalyst such, for example, as sulfuric acid, hydrochloric acid, organic sulfonic acids, acidic clays, acidic ion exchange resins, trifluoroacetic acid, trichloroacetic acid, fluoboric acid and the like. It should be noted, at this point that the above described reaction procedures for preparing these novel derivatives will often yield mixtures of two or more ureidoalkylphosphonates.

The novel ureidoalkylphosphonates of this invention are, in general, viscous liquids or low melting thermoplastic resinous solids. Usually they are soluble in water and in alcohols. In some cases, especially where $R_1R_2$, $R_3$ and $R_4$, as defined above, are not hydroxymethyl, they are soluble in less polar organic solvents such as toluene, xylene, mineral spirits, esters, such as ethyl acetate, ketones such as acetone or isophorone and chlorinated hydrocarbons such as chloroform and are, thus, compatible with organic solvent-based coating and ink formulations as well as with non-aqueous textile finishing formulations.

The ureidoalkylphosphonates of this invention where at least one of the $R_1$, $R_2$, $R_3$ or $R_4$ groups is a methylol or a $C_1$–$C_{12}$ alkoxymethyl group and where at least one additional $R_1$, $R_2$, $R_3$ or $R_4$ group is hydrogen, methylol or $C_1$–$C_{12}$ alkoxymethyl are self-curable forming crosslinked resins under acid catalyzed conditions. Suitable acid catalysts for this purpose include sulfuric acid, hydrochloric acid, phosphoric acid, p-toluenesulfonic acid, methanesulfonic acid, trichloroacetic acid, trifluoroacetic acid, alkyl acid phosphates and the like. Furthermore, all of the ureidoalkylphosphonates of this invention are co-curable with aminoplast-forming co-reactants, under acid catalyzed conditions, forming flame retardant, crosslinked resin products having durably bonded phosphorus, useful as textile finishes, coatings, laminates, adhesives and moldings.

Suitable aminoplast-forming co-reactants include ureaformaldehyde condensation products, melamine-formaldehyde condensation products, and urea-glyoxal-formaldehyde condensation products.

The products of the invention can also be co-cured with phenol-formaldehyde or with furfural condensation products or with alkyd resins, or with thermosetting acrylic resins so as to form flame retardant, crosslinked resins having durably bound phosphorus, useful in textile finishes, coatings, laminates, adhesives and moldings.

As has already been noted, hereinabove, the ureidoalkylphosphonates of this invention provide excellent results when utilized as flameproofing finishes for flammable substrates such as paper and for both natural and synthetic textile materials. It is also noteworthy to point out that the textile finishes derived from these derivatives may also be characterized as "durable press" finishes since they permit the textile to which they have been applied to retain their original shape and remain wrinkle-free after being laundered without any need for having them ironed.

Textiles may be treated with the derivatives of the invention while the latter are dissolved in an aqueous medium. And, where $R_1$, $R_2$, $R_3$ and $R_4$, as defined above, are not hydroxymethyl, they may be applied while in the form of hydrocarbon, organic solvent solutions utilizing such essentially non-polar solvents as methylene chloride, ethylene dichloride, trichlorethane, perchloroethylene, etc. and mixtures thereof. This ability to employ the ureidoalkylphosphonates of this invention in organic solvent media, the use of which is becoming increasingly more important in the textile finishing art, represents a distinct advantage with respect to the flame retardant, phosphorus containing urea derivatives of the prior art which generally lacked organic solvent solubility.

The solutions, either aqueous or organic solvent, containing one or more of the ureidoalkylphosphonate derivatives of this invention, may be applied to textiles by the use of any desired procedure. It is merely necessary to have the ureidoalkylphosphonate absorbed throughout the mass of the textile and/or to apply it to at least one surface thereof by means of any convenient procedure. Thus, they may be applied by being sprayed onto one or both surfaces of the textile or, as is more frequently the case, the textile may be passed or padded through the solution while the latter is being held in a tank or other suitable container. Such a process is commonly referred to as a "padding" technique with the solution being referred to as a "padding bath" or "padding solution".

The concentration of the ureidoalkylphosphonate within the padding bath, or other applicable solution, will be dependent upon a number of factors including the nature of the fibers which comprise the textile, the weight and weave of the textile, the degree of flameproofing that is desired in the finished textile, as well as other technical and economic considerations known and understood by those skilled in the art. However, it is generally desirable that the padding bath should contain from about 5 to 75%, by weight, of one or more of the ureidoalkylphosphonate; the latter concentration being sufficient to deposit a finish upon the textile which will contain from about 5 to 75%, by weight, of the uredioalkylphosphonate which, in turn, will provide the thus treated textile with about 0.2 to 7.5%, by weight, of the textile, of phosphorus. Again, it is to be stressed that the latter limits are merely illustrative and may be varied so as to provide a textile finish having any desired degree of flame retardancy.

Subsequent to their deposition upon and/or their absorption by a textile, the ureidoalkylphosphonates contained within the padding solution may be cured, or crosslinked, so as to yield a highly durable, fire retardant finish. This curing operation may be accomplished by air drying the treated fabric for a period of from about one to 10 days at ambient temperature, or, a more rapid cure may be affected by the application of heat at temperatures of up to about 200° C. Under the latter conditions, a curing time as short as only about one second may be required. Additional control of the curing rate may be achieved by the optional presence in the padding solution of pH controlling substances such as acid releasing salts which accelerate or catalyze the rate of cure or basic substances which will, on the other hand, retard the cure rate.

Rate retarding substances include, for example, alkali metal hydroxides, such as sodium hydroxide; and alkali metal bicarbonates and carbonates such as sodium bicarbonate and sodium carbonate. Cure accelerators, or catalysts, are exemplified by ammonium, alkaline earth and transition metal salts such as ammonium chloride, magnesium cloride, zinc chloride and zinc nitrate; amine hydrochlorides such as diethanolamine hydrochloride triethyleneamine hydrochloride; and, organic and inorganic acids such as acetic, oxalic, maleic, malic, citric, trichloroacetic, hydrochloric and phosphoric acids and alkyl acid phosphates. These optional curing rate retarders and accelerators may, respectively, be used alone or in combination with one aother in a concentration which is sufficient to attain the cure rate desired by the practitioner.

Another class of optional adjuvants which may be included within the solutions containing the ureidoalkylphosphonate derivatives of this invention, when the latter are being used for the preparation of flame retardant textile finishes, are various so-called co-reactants. These co-reactants are materials which will undergo a reaction with the ureidoalkylphosphonate and which are used for various purposes such as to control the cross-link density of the finish, to improve the hand and durability of the finished textile as well as its durability, flame retardance, durable press, laundering and crease resistance properties. Particularly useful as co-reactants are aminoplastic-forming reagents such, for example, as urea; condensation products of ureaformaldehyde, urea-glyoxal or urea-glyoxal-formaldehyde; melamine; melamine-formaldehyde condensation products; N-methylolated o-alkyl carbamates; ammonia, and formaldehyde. Each of the above described co-reactants are capable of use either alone or admixed with one another. It is to be understood, that the use, in the above given list, of the term "urea" is meant to include within its scope various cyclic ureas such, for example, as ethyleneurea, propyleneurea, uron, triazones, glyoxaldiurein and isocyanuric acid.

Other suitable co-reactants include formamide, acetamide, propionamide, dialkoxyphosphonopropionamide or the N-methylol derivatives thereof, tetrakis(hydroxymethyl) phosphonium chloride or hydroxide, trimethylol phosphine, aminated phosphonitrilic chloride, phosphoric triamide and thermal condensation products thereof, ammonium phosphates, glycols such as the phosphorus-containing glycols and the hydroxyalkyl esters of all phosphorus acids. Particularly useful as co-reactants are the novel triazinylamino phosphonates disclosed in copending application Ser. No. 50,364 filed June 26, 1970, now U.S. Pat. No. 3,755,532, In general, the ureidoalkylphosphonate finishing reagents of this invention can be made to condense during the above described curing process with co-reactant compounds having either —OH, —NH, or —N-CH$_2$OCH$_3$ groups and the proper selection of such co-reactants in order to achieve a desired modification of cross-link density, crease resistance, durable press, and flame retardant properties will be evident to those skilled in the art. Some specific co-reactants which may be named are: dimethylolmelamine; trimethylolmelamine; dimethylol dihydroxyethyleneurea; trismethoxymethylmelamine; dimethyloluron; dimethylolethyleneurea; dimethylolpropyleneurea; N,N-dimethylol methyl carbamate; N,N-dimethylol 2-hydroxyethylcarbamate; N,N-dimethylol ethyl carbamate; N,N-dimethylol methoxyethylcarbamate; methylolurea; dimethylolurea; partially methylated pentamethylolmelamine; tetramethylolglyoxaldiurein; N-methylol-2-(dimethoxyphosphono)propionamide; and, N-methylolacrylamide.

Various other classes of optional adjuvants may also be present in the textile finishing solutions of this invention. Thus, the padding bath containing the ureidoalkylphosphonates of this invention and the textile finishes derived, therefrom, may contain other ingredients in order to modify the finish in accordance with practices known to those skilled in the art of textile finishings.

For example, these other ingredients may include hand modifiers such as polyethylene emulsions, long chain fatty amides, paraffin waxes, long chain quaternary ammonium salts, and the like; auxiliary flame retardants such as chloroparaffins, chlorinated polyethylene, polyvinyl chloride, polyvinylidene chloride, homo- or copolymers of vinyl phosphonates and antimony compounds such as antimony oxide, antimony phosphate, and the like; soil release, anti-soiling agents and water and oil-repellents such as polyfluoroalkyl compounds, silicones, acrylic acid copolymers, and the like; abrasion resistance agents such as polyacrylates, polyurethanes, and the like; colorants and color-modifying agents such as dyes, pigments, bleaches, anti-fading agents, ultraviolet screening agents and the like; anti-static agents such as quaternary ammonium compounds; humectants; bonding agents; antimicrobial agents which will supplement the inherent rot-resistance and antimicrobial action of the ureidoalkylphosphonate containing finishes of this invention; and pH modifying agents. The padding bath may also contain adjuvants intended to directly facilitate the padding operation per se, such as emulsifying and wetting agents, swelling agents, and buffers.

Although the novel finishes of this invention are most notably effective on cellulosic textiles, nonetheless all types of textiles may be treated by means of the process of this invention so as to provide them with durable, fire retardant finishes. Thus, one may treat textiles derived from natural fibers such as cotton, wool, silk, sisal, jute, hemp and linen and from synthetic fibers including nylon and other polyamides; polyolefins such as polypropylene; polyesters such as polyethylene terephthalate; cellulosics such as rayon, cellulose acetate and triacetate; fiber glass; acrylics and modacrylics, i.e. fibers based on acrylonitrile copolymers; saran fibers, i.e. fibers based on vinylidene chloride copolymers; nytril fibers, i.e. fibers based on vinylidene dinitrile copolymers; rubber based fibers; spandex fibers, i.e. fibers based on a segmented polyurethane; vinal fibers, i.e. fibers based on vinyl alcohol copolymers; vinyon fibers, i.e. fibers based on vinyl chloride copolymers; and metallic fibers. Textiles derived from blends of any of the above listed natural and/or synthetic fibers may also be treated by means of the process of this invention.

As used in this disclosure, the term "textile" or "textiles" is meant to encompass woven or knitted fabrics as well as non-woven fabrics which consist of continuous or discontinuous fibers bonded so as to form a fabric by mechanical entanglement, thermal interfiber bonding or by use of adhesive or bonding substances. Such non-woven fabrics may contain a certain percentage of wood pulp as well as conventional textile fibers in which case part of the bonding process is achieved by means of hydrogen bonding between the cellulosic pulp fibers. In non-woven fabrics, the finishing agents of this invention can serve not only as flame retardant finishes but can also contribute to the interfiber bonding mechanism by serving as all or part of the adhesive or bonding resin component. This dual role can also be played by the finishing agents of this invention in fabric laminates where the finishing agent can at the same time serve as the interlaminar bonding agent and as the flame retardant. In both of these systems, i.e. non-woven fabrics and laminated fabrics, the finishing agents of this invention can also be blended with the usual bonding agents such, for example, as acrylic emulsion polymers, vinyl acetate, homo- and copolymer emulsions, styrenebutadiene rubber emulsions, urethane resin emulsions, polyvinylchloride emulsions, polyvinylchloride-acrylate emulsions, polyacrylates modified by vinyl carboxylic acid comonomers and the like.

In addition to being used for the preparation of fire retardant textile finishes, the novel ureidoalkylphosphonates of the invention may also be used in various other applications in which their flame retardant properties are advantageous. These include their being cured or co-cured with co-reactants as named above into thermoset resins which may be employed for the preparation of molded objects and coatings or for laminating or impregnating paper and wood, or as adhesives. In molding applications, fillers such as wood flour, clays, mica and the like are often advantageously employed. The resins of the invention in either uncured or thermoset form may also be used as flame retardant additives for other resins.

The following examples further illustrate the embodiment of this invention. In these examples all parts given are by weight unless otherwise noted.

EXAMPLE I

This example illustrates the preparation of one of the novel ureidoalkylphosphonates of this invention by means of the reaction of trimethyl phosphite with dimethylolurea.

A mixture of 24g. (0.2 mole) of commercial dimethylolurea and 100g. of redistilled trimethyl phosphite was stirred and heated at 100° C. over a 1 hour period with substantially all of the theoretical amount of methanol being removed with a fractionating column. The reaction mixture was then heated to 133° C., subsequently cooled and stripped free of excess trimethyl phosphite to a pot temperature of 137" and final vacuum of 1.5mm. The residual product comprised 55g. (92% yield) of a viscous, nearly colorless syrup which was soluble in water and chloroform. The infrared spectrum showed NH (3320), C=O (1675-1690), NH (1568), P=O (1230-1260 cm$^{-1}$). The nuclear magnetic resonance spectrum showed two types of CH$_3$OP groups and P-CH$_2$ groups in an incompletely resolved multiplet at 3.7 ppm as well as NH at 6.6, the area ratio of CH to NH corresponding to the theoretical for a

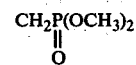

urea substituted by two groups. The presence of two types of CH$_3$OP groups suggests that both N,N' and N,N-disubstituted structures are present as follows:

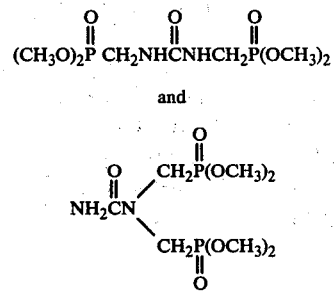

Anal. Calcd. for C$_7$H$_{18}$O$_7$P$_2$N$_2$:P 20.4, N 9.2 Found: P 19.5, N 9.4

A small amount of —NH-CH$_2$O—structures may also be present, indicated by an n.m.r. signal at 4.36 ppm.

EXAMPLE 2

This example illustrates the preparation of one of the novel ureidoalkylphosphonates of this invention by means of the reaction of triethyl phosphite with dimethylolurea.

In a similar manner to Example 1, hereinabove dimethylolurea was reacted with triethyl phosphite. The product was a pale yellow syrup the n.m.r. spectrum of which showed NH, CH$_3$, and CH$_2$ bands in an area ratio of 1.7:12:12. Theoretical for urea substituted by two

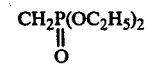

groups, 2:12:12.

Anal. Calcd. for C$_{11}$H$_{26}$O$_7$P$_2$N$_2$:P 14.9, N 6.7 Found: P 13.5, N 5.9

EXAMPLE 3

This example illustrates the use of one of the novel ureidoalkylphosphonates of this invention for the flameproofing of textiles:

A padding bath was formulated as follows:

|  | Parts |
| --- | --- |
| The product of Example 1, hereinabove | 9.2 |
| Hexamethoxymethylmelamine | 12.0 |
| Zinc nitrate (catalyst) | 0.2 |
| Octylphenoxypolyethoxyethanol (a non-ionic surfactant) | 0.02 |
| Plus sufficient water to provide total of 50 parts by weight. | |

A sample of 8 ounce cotton cloth was treated with this solution at a 70%, by weight, wet add-on and a 25%, by weight, dry add-on. After curing at 160° C. for 5 minutes, it was found to be self-extinguishing when ignited and useful self-extinguishing properties persisted after laundering. The cloth contained 1.4%, by weight, of phosphorus after hot water washing and 0.7%, by weight, of phosphorus after soda ash-soap laundering at 100° C.

EXAMPLE 4

This example illustrates the preparation of the monomethylol derivatives of the ureioalkylphosphonates whose respective preparation is illustrated in Examples 1 and 2 hereinabove.

(A) To a solution of 18 parts of the product of Example 1 in 12 parts of water there was added 4.9 parts of 37% aqueous formaldehye. The pH was adjusted to 9.4–9.5 and held for 1 hr. at this level by the periodic addition of aqueous NaOH. Finally, the pH was adjusted to 6.9 by the dropwise addition of concentrated hydrochloric acid. The solution was then made up to a total of 100 parts by weight by adding water.

(B) In a similar manner, 21.7 parts of the product of Example 2 was reacted with formaldehyde in a 2% excess over equimolar.

It was then made up to a total of 65.5 parts with additional water. In both instances, the reaction of the major part of the formaldehyde was established by assaying th finished solution for unreacted formaldehyde.

EXAMPLE 5

This example illustrates the use, for the flameproofing of textiles, of the monomethylated derivative whose preparation was described in part (A) of Example 4, hereinabove.

A padding bath was prepared by blending the solution of the monomethylated product of Example 2, whose preparation was described in Part A of Example 4, with 4.75 parts of pentamethylolmelamine, 0.95 parts of urea, 0.4 parts of ammonium chloride as a catalyst and 0.2 parts of octylphenoxypolyethoxyethanol. The bath was then made up to a total of 95 parts by adding water. Eight ounce cotton cloth was padded in this solution, dried, cured at 165° C. for 10 minutes and washed. It was found to be self-extinguishing when ignited in air.

EXAMPLES 6–15

These examples are illustrative of the preparation of additional species of the novel ureidoalkylphosphonates of this invention.

Following the procedure of Example 1, hereinabove, various ureidoalkylphosphonates were prepared by means of the respective reactions beween a number of different urea intermediates and phosphorus containing reactants. The following table describes the thus prepared ureidoalkylphosphonates and provides all of the information relating to the process conditions and reagents utilized for their preparation.

| EXAMPLE NO. | UREA INTERMEDIATE | PHOSPHORUS REACTANT | REACTION CONDITIONS | PROPOSED STRUCTURE OF PRINCIPAL PRODUCT | CHARACTER OF PRODUCT |
|---|---|---|---|---|---|
| 6 | (structure) | $P(OC_2H_5)_3$ (1 equiv.) | Reflux in toluene and distill off 1 equivalent of ethanol | (structure) | Water-soluble resin containing no trivalent P. |
| 7 | (structure) | $P(OCH_3)_3$ (1 equiv.) | Reflux in methanol until free of trivalent phosphorus by means of $HCl_2$ reduction test | (structure) | " |
| 8 | (structure) | $P(OCH_3)_3$ (2 equiv.) | Reflux in dioxane and fractionally distill 1 equivalent of methanol | (structure) | " |
| 9 | (structure) | $HP(OC_2H_5)_2$ (1 equiv.) | Slowly increase temp. from 20 to 130° C. over 10 hrs. allowing distillation of alcohol to take place. | (structure) | " |
| 10 | (structures) | $HP(OC_2H_5)_2$ (1 equiv.) | Reflux in ethanol until infrared analysis for P-H is negative | (structures) | " |
| 11 | (structure) | $P(OC_2H_5)_3$ (1 equiv.) | Reflux in toluene and fractionate off one equivalent of ethanol | (structure) | " |

-continued

| EXAMPLE NO. | UREA INTERMEDIATE | PHOSPHORUS REACTANT | REACTION CONDITIONS | PROPOSED STRUCTURE OF PRINCIPAL PRODUCT | CHARACTER OF PRODUCT |
|---|---|---|---|---|---|
| 12 | (structure) | $HOCH_2P(OC_2H_5)_2$, O (1 mole) | Reflux in benzene with a 1%, by wt. of a sulfuric acid cat., then fractionate off water. | (structure) | " |
| 13 | (structure) | $HOCH_2P(OCH_3)_2$, O (1 equiv.) | Reflux in toluene with 1%, by wt., of toluene-sulfonic acid; then fractionate off $CH_3OH$. | (structure) | " |
| 14 | (structure) | $HP(OCH_3)_2$, O (1 equiv.) | Heat slowly to 130° C. allowing one equivalent of alcohol to distill off. | (structure) | " |
| 15 | (structure) | $HP(OC_2H_5)_2$, O (1 equiv.) | Heat slowly to 130° C. allowing one equivalent of alcohol to distill off. | (structure) | |

EXAMPLE 16

This example illustrates the use of one of the novel ureidoalkylphosphonates of this invention for the flame-proofing of textiles. A padding bath containing the following ingredients was prepared.

|  | Parts |
| --- | --- |
| Product of Example 1 | 6.08 |
| Pentamethylolmelamine | 2.3 |
| Zinc nitrate (catalyst) | 0.5 |
| Octylphenoxypolyethoxyethanol | 0.05 | plus enough H₂O to provide a total a total of 12.4 parts by weight.

Eight ounce cotton cloth was padded in this solution, dried for ½ hour at ambient temperature and then cured for 5 minutes at 160° C. It was then washed in warm running water and dried. The cloth was found to contain 1.50%, buy weight, of phosphorus. An accelerated laundering test, comprising 3 hrs. of boiling with 0.5%, by weight, of soap in a 0.2%, by weight, sodium carbonate solution only lowered the phosphorus content to 1.40%, by weight, and the cloth remained flame retardant.

EXAMPLE 17

This example illustrates the use of another of the novel ureidoalkylphosphonates of this for the flame-proofing of textiles.

A padding bath containing the following ingredients was prepared:

|  | Parts |
| --- | --- |
| The product of Example 6 | 20 |
| Trimethylolmelamine | 20 |
| Magnesium chloride | 2 |
| Octylphenoxypolyethoxyethanol | 0.2 | plug enough H₂O to provide a total of 100 parts by weight.

Eight ounce cotton twill cloth was padded to an 80%, by weight, uptake, dried, and cured at 165° C. for 5 minutes and then washed. The fabric was found to have durable press properties and was self-extinguishing when ignited in air.

EXAMPLE 18

This example illustrates the use of another of the novel ureidoalkylphosphonates of this invention for the flame-proofing of textiles.

A padding bath containing the following ingredients was prepared:

|  | Parts |
| --- | --- |
| Product of Example 9 | 20 |
| Dimethyloldihyroxyethyleneurea | 20 |
| Zinc nitrate (catalyst) | 2 |
| Octylphenoxypolyethoxyethanol | 0.1 | plug enough water to provide a total of 100 parts.

A 70:30 cotton/polyester blend cloth was padded in this bath, dried and cured at 155°-160° C. for 3 minutes. The fabric was found to have durable press properties and was self-extinguishing when ignited in air.

EXAMPLE 19

This example illustrates the use of one of the novel ureidoalkylphosphonates of this invention for the impregnation of paper.

A mixture of 6.1 parts of the product of Example 1, 18.3 parts of hexamethoxymethylmelamine and 0.05 parts of zinc nitrate was impregnated into porous paper and cured by heating at 150° C. The resultant resin impregnated paper was rapidly self-extinguishing when ignited in air, even after soaking in running water for 5 hours.

EXAMPLE 20

This example illustrates the preparation of another of novel derivatives of this invention. To 190g. (1 mole) of bis(methoxymethyl)uron, there was added 136g. (1.1 mole) of trimethyl phosphite and the mixture was then treated dropwise, with stirring at 28°-32° C., with 45.8g. (0.33 mole) of phosphorus trichloride which had been diluted with 50cc. of toluene. After a three hour addition period, the mixture was left standing overnight. Mercurometric assay showed that about 0.1 mole of trimethyl phosphite remained unreacted. Stripping to 70° C./0.1 mm. removed the methyl chloride, the toluene and the excess trimethyl phosphite, leaving behind 265g. of the desired product having the formula:

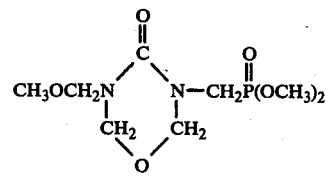

which was in the form of a colorless viscous, water-soluble syrup having no residual trivalent phosphorus as determined by mercurimetric, (HgCl₂), assay.

Variations may be made in proportions, procedures and materials without departing from the scope of this invention as defined in the following claims.

What is claimed is:

1. The ureidoalkylphosphonates selected from the group consisting of:

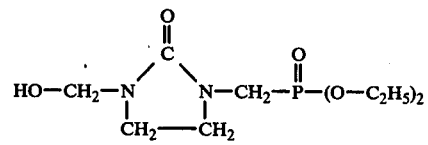

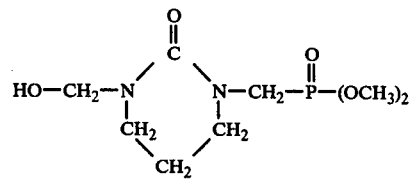

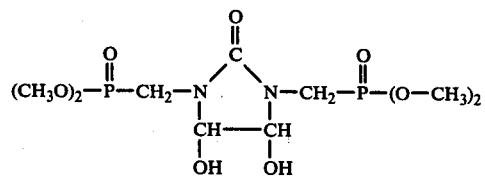

-continued
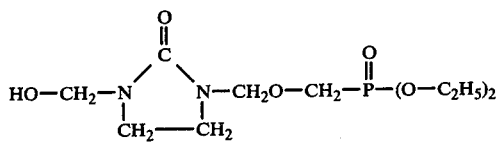
-continued
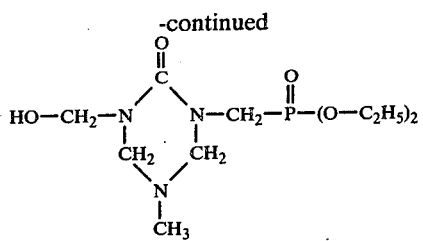
2. A ureidoalkylphosphonate corresponding to the formula:
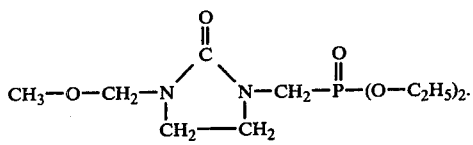
* * * * *

UNITED STATES PATENT AND TRADEMARK OFFICE
CERTIFICATE OF CORRECTION

PATENT NO. : 4,145,547
DATED : March 20, 1979
INVENTOR(S) : Edward D. Weil

It is certified that error appears in the above-identified patent and that said Letters Patent are hereby corrected as shown below:

Col. 3, line 16, change "Process No. a" to -- Process No. 1a"--

Col. 4, line 40, change "$<$CHCH$>$" to -- $>$CHCH$<$ --

Col. 5, line 3, change "$<$CHCH$>$" to -- $>$CHCH$<$ --

Col. 5, line 20, change "di-2hydroxyethyl" to -- di-2-hydroxyethyl

Col. 7, line 44, change "aother" to -- another --

Col. 9, line 13, change "vinal" to -- vinyl --

Col. 10, line 8, change " 137" to -- 137° --

Col. 11, line 26, change "ureioalkylphosphonates" to -- ureidoalkylphosphonates --

Col. 12, line 9 change "th" to -- the --

Col. 13, Example 6 change formula

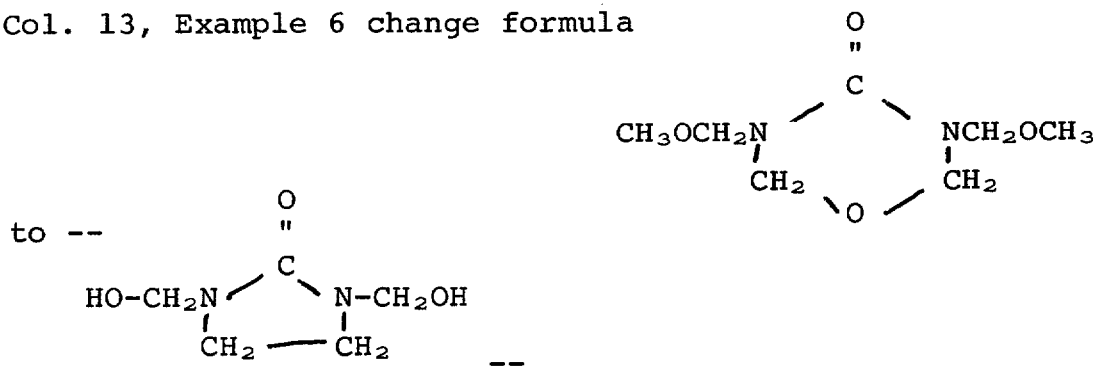

UNITED STATES PATENT AND TRADEMARK OFFICE
CERTIFICATE OF CORRECTION

PATENT NO. : 4,145,547

DATED : March 20, 1979

INVENTOR(S) : Edward D. Weil

It is certified that error appears in the above-identified patent and that said Letters Patent are hereby corrected as shown below:

Col. 13 under Reaction Conditions, change "$HCl_2$" to -- $HgCl2$ --

Col. 17, line 15, after "a total" first occurrence, delete second -- a total --

Col. 17, line 21, change "buy weight" to -- by weight --

Col. 17, line 30, add the word -- invention -- after this

Col. 17, line 41, change "plug" to -- plus --

Col. 17, line 64, change "plug" to -- plus --

Col. 13, example 9, change formula : " 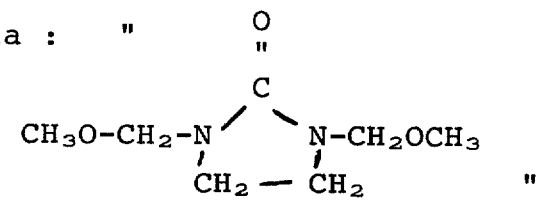

to -- 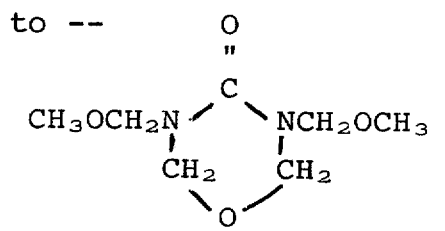 --

Signed and Sealed this

Fourth Day of September 1979

[SEAL]

Attest:

Attesting Officer

LUTRELLE F. PARKER
*Acting Commissioner of Patents and Trademarks*